United States Patent
Dunkley et al.

(12)

(10) Patent No.: US 11,484,671 B2
(45) Date of Patent: **\*Nov. 1, 2022**

(54) AEROSOLIZATION APPARATUS WITH CAPSULE PUNCTURE ALIGNMENT GUIDE

(71) Applicant: BGP Products Operations GmbH, Allshwill (CH)

(72) Inventors: Michael John Dunkley, Nottingham (GB); Jon David Tuckwell, Cambridgeshire (GB); Edward William Vernon-Harcourt, Cambridge (GB); Mark Glusker, San Mateo, CA (US); Steve Paboojian, Menlo Park, CA (US)

(73) Assignee: BGP Products Operations GmbH

( * ) Notice: Subject to any disclaimer, the term of this patent is extended or adjusted under 35 U.S.C. 154(b) by 212 days.

This patent is subject to a terminal disclaimer.

(21) Appl. No.: 16/259,492

(22) Filed: Jan. 28, 2019

(65) Prior Publication Data

US 2020/0197636 A1 Jun. 25, 2020

Related U.S. Application Data

(63) Continuation of application No. 10/821,624, filed on Apr. 9, 2004, now Pat. No. 10,207,066.
(Continued)

(51) Int. Cl.
*A61M 15/00* (2006.01)

(52) U.S. Cl.
CPC .... *A61M 15/0028* (2013.01); *A61M 15/0033* (2014.02); *A61M 2202/064* (2013.01)

(58) Field of Classification Search
CPC .......... A61M 15/0028; A61M 15/0033; A61M 15/0035; A61M 15/0041; A61M 2202/064
See application file for complete search history.

(56) References Cited

U.S. PATENT DOCUMENTS

| 154,864 A | 9/1874 | Harvey |
|---|---|---|
| 2,151,418 A | 5/1937 | Bolte |

(Continued)

FOREIGN PATENT DOCUMENTS

| EP | 0666085 A1 | 8/1995 |
|---|---|---|
| EP | 0753319 A1 | 1/1997 |

(Continued)

OTHER PUBLICATIONS

Mienkin et al., "Drug Emission Efficacy of Turbospin a New Single Dose Dry Powder Inhaler," 14th Pharmaceutical Technology Conference, Barcelon, Spain, Apr. 4-6, 1995.

*Primary Examiner* — Kathryn E Ditmer

(57) ABSTRACT

An aerosolization apparatus comprises a housing defining a chamber having one or more air inlets. The chamber is sized to receive a capsule which contains an aerosolizable pharmaceutical formulation. The aerosolization apparatus further comprises a puncturing mechanism within the housing. The puncturing mechanism comprises an alignment guide and a puncture member, wherein the alignment guide comprises a surface adapted to contact the capsule while the puncture member is advanced into the capsule to create an opening in the capsule. At least a portion of the surface is sloped relative to the longitudinal axis of the capsule. Alternatively or additionally, the surface may comprise one or more protrusions. An end section is associated with the housing. The end section is sized and shaped to be received in a user's mouth or nose so that the user may inhale through the end section to inhale aerosolized pharmaceutical formulation that has exited the capsule through the opening created in the capsule. The alignment guide allows for more consistent puncturing of the capsule and a longer lifetime of the apparatus.

20 Claims, 4 Drawing Sheets

Related U.S. Application Data

(60) Provisional application No. 60/461,748, filed on Apr. 9, 2003.

(56) References Cited

U.S. PATENT DOCUMENTS

| | | | |
|---|---|---|---|
| 3,795,244 A | 3/1974 | Lax et al. | |
| 3,949,751 A * | 4/1976 | Birch | A61M 15/0028 128/203.15 |
| 3,991,761 A * | 11/1976 | Cocozza | A61M 15/0033 128/203.15 |
| 4,069,819 A * | 1/1978 | Valentini | A61M 15/0028 128/203.15 |
| 4,114,615 A | 9/1978 | Wetterlin | |
| 4,161,516 A | 7/1979 | Bell | |
| 4,247,066 A | 1/1981 | Frost et al. | |
| 4,338,931 A | 7/1982 | Cavazza | |
| 4,641,644 A | 2/1987 | Andersson et al. | |
| 4,846,876 A | 7/1989 | Draber et al. | |
| 4,884,565 A * | 12/1989 | Cocozza | A61M 15/0033 128/203.21 |
| 4,995,385 A | 2/1991 | Valentini et al. | |
| 5,301,666 A | 4/1994 | Lerk et al. | |
| 5,320,095 A * | 6/1994 | Nijkerk | A61M 15/0028 128/203.15 |
| 5,379,763 A | 1/1995 | Martin | |
| 5,447,151 A | 9/1995 | Bruna et al. | |
| 5,458,135 A | 10/1995 | Patton | |
| 5,505,194 A | 4/1996 | Adjei et al. | |
| 5,619,985 A | 4/1997 | Ohki et al. | |
| 5,645,050 A | 7/1997 | Zierenberg et al. | |
| 5,699,789 A | 12/1997 | Hendricks | |
| 5,727,546 A | 3/1998 | Clarke et al. | |
| 5,785,049 A | 7/1998 | Smith et al. | |
| 5,797,391 A | 8/1998 | Cook et al. | |
| 5,881,719 A | 3/1999 | Gottenauer et al. | |
| 5,896,855 A * | 4/1999 | Hobbs | A61M 15/0073 128/203.15 |
| 5,901,703 A | 5/1999 | Ohki et al. | |
| D410,541 S | 6/1999 | Moulin | |
| 5,921,236 A | 7/1999 | Ohki et al. | |
| 5,922,675 A | 7/1999 | Baker et al. | |
| 5,989,217 A | 11/1999 | Ohki et al. | |
| D420,736 S | 2/2000 | Moulin | |
| 6,123,070 A * | 9/2000 | Bruna | A61M 15/0065 128/203.12 |
| 6,230,707 B1 | 5/2001 | Horlin | |
| 6,257,233 B1 | 7/2001 | Burr et al. | |
| 6,298,846 B1 * | 10/2001 | Ohki | A61M 15/0028 128/203.15 |
| 6,357,490 B1 | 3/2002 | Johnston et al. | |
| 6,408,846 B1 * | 6/2002 | Ohki | A61M 15/0028 128/203.15 |
| 6,440,690 B1 * | 8/2002 | Mor | A61K 38/1703 435/32 |
| 6,470,884 B2 | 10/2002 | Horlin | |
| 7,278,425 B2 | 10/2007 | Edwards et al. | |
| 8,069,851 B2 | 12/2011 | Dunkley et al. | |
| 2002/0017295 A1 | 2/2002 | Weers et al. | |
| 2002/0121277 A1 | 9/2002 | Pera | |
| 2003/0000523 A1 | 1/2003 | Citterio | |
| 2004/0149283 A1 * | 8/2004 | Hochrainer | A61M 15/0033 128/203.15 |
| 2005/0051166 A1 * | 3/2005 | Glusker | A61M 15/0041 128/203.21 |
| 2005/0056280 A1 * | 3/2005 | Alston | A61M 15/0031 128/203.21 |

FOREIGN PATENT DOCUMENTS

| | | |
|---|---|---|
| WO | 9503846 A1 | 2/1995 |
| WO | 9524183 A1 | 9/1995 |
| WO | 9632096 A1 | 10/1996 |
| WO | 9632149 A1 | 10/1996 |
| WO | 9727892 A1 | 8/1997 |
| WO | 9742992 A1 | 11/1997 |
| WO | 9916419 A1 | 4/1999 |
| WO | 9916422 A1 | 4/1999 |
| WO | 9945987 A1 | 9/1999 |
| WO | 9007572 A2 | 2/2000 |
| WO | 9072904 A1 | 12/2000 |
| WO | 92083220 A2 | 10/2002 |

\* cited by examiner

AEROSOLIZATION APPARATUS WITH CAPSULE PUNCTURE ALIGNMENT GUIDE

This application claims the benefit U.S. Provisional Patent Application Ser. No. 60/461,748 filed on Apr. 9, 2003, which is incorporated herein by reference in its entirety.

BACKGROUND

The need for effective therapeutic treatment of patients has resulted in the development of a variety of techniques for delivering a pharmaceutical formulation to a patient. One traditional technique involves the oral delivery of a pharmaceutical formulation in the form of a pill, capsule, or the like. Inhalable drug delivery, where an aerosolized pharmaceutical formulation is orally or nasally inhaled by a patient to deliver the formulation to the patient's respiratory tract, has also proven to be an effective manner of delivery. In one inhalation technique, a pharmaceutical formulation is delivered deep within a patient's lungs where it may be absorbed into the blood stream. In another inhalation technique, a pharmaceutical formulation is delivered locally to a particular site, such as an infected lung. Many types of inhalation devices exist including devices that aerosolize a dry powder pharmaceutical formulation.

One type of inhalation device aerosolizes a pharmaceutical formulation that is stored in a capsule. For example, a dose or a portion of a dose of a dry powder pharmaceutical formulation may be stored in a capsule, and the capsule may be inserted into an aerosolization device which is capable of aerosolizing the pharmaceutical formulation. The aerosolization may be accomplished by releasing stored energy. For example, the aerosolization may be accomplished by utilizing energy supplied during the user's inhalation, such as the flow of inhaled air, to aerosolize the pharmaceutical formulation.

Before, during or after being inserted into the aerosolization device, the capsule is opened to expose the pharmaceutical formulation. The opening of the capsule may be performed, for example, by puncturing the capsule, tearing the capsule, or separating the parts of the capsule. When the capsule is properly opened and when aerosolization energy is supplied, the pharmaceutical formulation is aerosolized so that it may be inhaled by the user and a dose or portion of a dose of the aerosolized pharmaceutical formulation may be delivered to the user's respiratory tract.

However, improper use of the aerosolization device may result in the delivery of less than the desired amount of the pharmaceutical formulation. For example, if a capsule is not properly or completely opened before the aerosolization process, the amount of pharmaceutical formulation being aerosolized may be reduced or the flow of the aerosolized pharmaceutical formulation may not be of sufficiently high quality to deliver a desirable amount to the user. In addition, residual pharmaceutical formulation within the aerosolization apparatus can limit the effectiveness of the capsule puncturing process.

Therefore, it is desirable to be able to improve the effectiveness and reproducibility of a capsule opening mechanism for an aerosolization apparatus. It is further desirable to be able to provide such capsule opening in a manner than increases the lifetime of the aerosolization apparatus.

SUMMARY

The present invention satisfies these needs. In one aspect of the invention, a capsule puncturing mechanism has a capsule alignment guide that improves the quality and consistency of capsule punctures. Additionally, the alignment guide extends the lifetime of the aerosolization apparatus.

In another aspect of the invention, an aerosolization apparatus comprises a housing defining a chamber having one or mom air in the chamber being sized to receive a capsule which contains an aerosolizable pharmaceutical formulation; a puncturing mechanism within the housing, the puncturing mechanism comprising an alignment guide and a puncture member, wherein the alignment guide comprises a surface adapted to contact the capsule while the puncture member is advanced into the capsule to create an opening in the capsule, and wherein at least a portion of the surface is sloped at an angle which is less than 55 degrees relative to the longitudinal axis of the capsule; and an end section associated with the housing, the end section sized and shaped to be received in a user's mouth or nose so that the user may inhale through the end section to inhale aerosolized pharmaceutical formulation that has exited the capsule through the opening created in the capsule.

In another aspect of the invention, an aerosolization apparatus comprises a housing defining a chamber having one or more air inlets, the chamber being sized to receive a capsule which contains an aerosolizable pharmaceutical formulation; a puncturing mechanism within the housing, the puncturing mechanism comprising an alignment guide and a puncture member, wherein the alignment guide comprises a surface adapted to contact the capsule while the puncture member is advanced into the capsule to create an opening in the capsule, and wherein the surface comprises one or more protrusions for contacting the capsule; and an end section associated with the housing, the end section sized and shaped to be received in a user's mouth or nose so that the user may inhale through the end section to inhale aerosolized pharmaceutical formulation that has exited the capsule through the opening created in the capsule.

In another aspect of the invention, a method of providing access to an aerosolizable pharmaceutical formulation comprises providing a capsule containing an aerosolizable pharmaceutical formulation; contacting the capsule with the surface of an alignment guide, the surface being sloped at an angle which is less than 55 degrees relative to the longitudinal axis of the capsule; and advancing a puncture member through the wall of the capsule to create an opening in the capsule.

In another aspect of the invention, a method of providing access to an aerosolizable pharmaceutical formulation comprises providing a capsule containing an aerosolizable pharmaceutical formulation; contacting the capsule with the surface of an alignment guide, the surface comprising one or more protrusions for contacting the capsule; and advancing a puncture member through the wall of the capsule to create an opening in the capsule.

In another aspect of the invention, a method of aerosolizing a pharmaceutical formulation comprises inserting a capsule containing an aerosolizable pharmaceutical formulation in a chamber; contacting the capsule with the surface of an alignment guide, the surface being sloped at an angle which is less than 55 degrees relative to the longitudinal axis of the capsule and/or having one or more protrusions for contacting the capsule; advancing a puncture member through the wall of the capsule to create an opening in the capsule; aerosolizing the pharmaceutical formulation in the capsule by flowing air through the chamber; and administering the aerosolized pharmaceutical formulation to the respiratory tract of a user during the user's inhalation.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to an aerosolization apparatus. In particular, the invention relates to an aerosolization apparatus capable of aerosolizing a powder contained in a capsule. Although the process is illustrated in the context of aerosolizing a dry powder pharmaceutical formulation for inhalation, the present invention can be used in other processes and should not be limited to the examples provided herein.

Figure 1A:
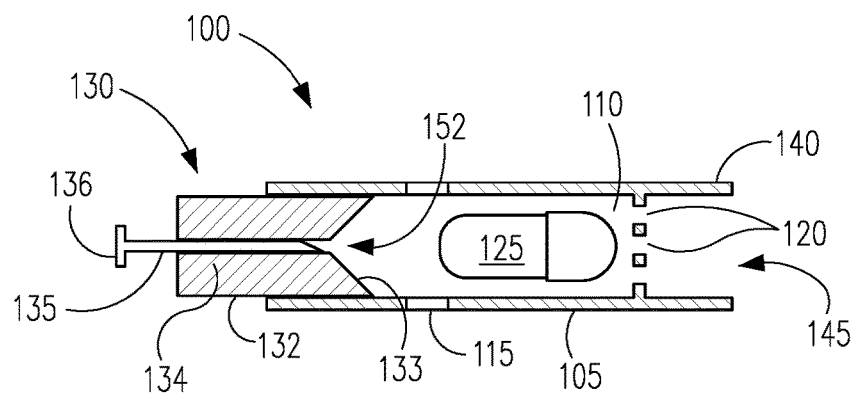
FIG. 1A is a schematic sectional side view of a version of an aerosolization apparatus in a rest position.
Figure 1B:
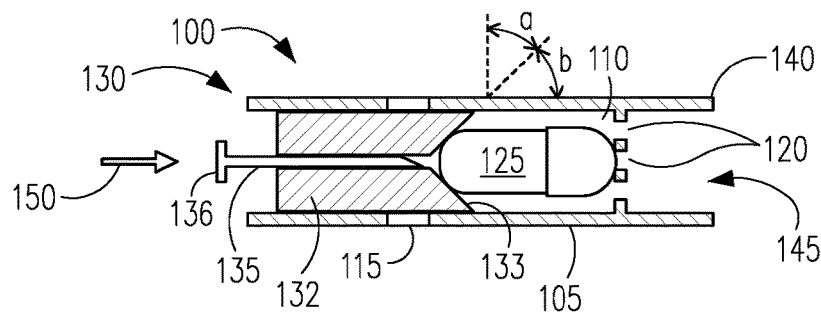
FIG. 1B is a schematic sectional side view of the version of an aerosolization apparatus shown in FIG. 1A just before capsule puncture.

An aerosolization apparatus 100 according to the present invention is shown schematically in FIG. 1A. The aerosolization apparatus 100 comprises a housing 105 defining a chamber 110 having one or more air inlets 115 and one or more air outlets 120. The chamber 110 is sized to receive a capsule 125 which contains an aerosolizable pharmaceutical formulation. A puncturing mechanism 130 comprises an alignment guide 132 having a seating surface 133 and a passageway 134 in which a puncture member 135 is slidably received. Near or adjacent the outlet 120 is an end section 140 that may be sized and shaped to be received in a user's mouth or nose so that the user may inhale through an opening 145 in the end section 140 that is in communication with the outlet 120.

The aerosolization apparatus 100 utilizes air flowing through the chamber 110 to aerosolize the pharmaceutical formulation in the capsule 125. For example, FIGS. 1A through 1E illustrate the operation of a version of an aerosolization apparatus 100 where air flowing through the inlet 115 is used to aerosolize the pharmaceutical formulation and the aerosolized pharmaceutical formulation flows through the outlet 120 so that it may be delivered to the user through the opening 145 in the end section 140. The aerosolization apparatus 100 is shown in its initial condition in FIG. 1A. The capsule 125 is positioned within the chamber 110 and the pharmaceutical formulation is contained within the capsule 125.

Figure 1C:
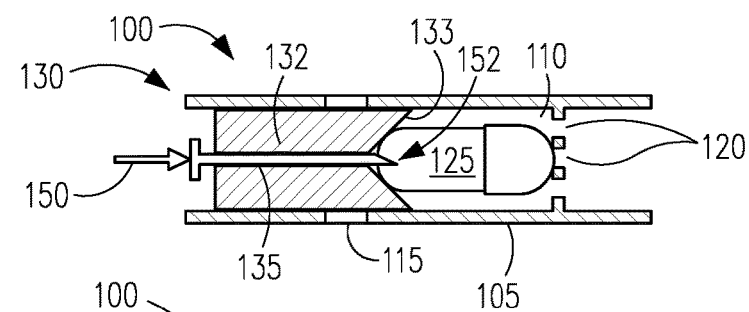
FIG. 1C is a schematic sectional side view of the version of an aerosolization apparatus shown in FIG. 1A as the capsule is being punctured.
Figure 1D:
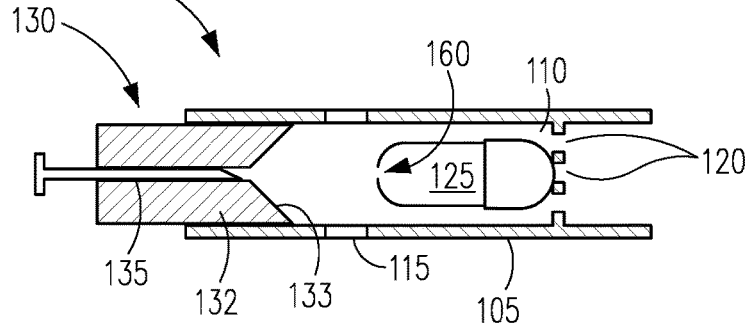
FIG. 1D is a schematic sectional side view of the version of an aerosolization apparatus shown in FIG. 1A just after capsule puncture.

To use the aerosolization apparatus 100, the pharmaceutical formulation in the capsule 125 is exposed to allow it to be aerosolized. In the version of FIGS. 1A though 1E, the puncture mechanism 130 is advanced within the chamber 110 by applying a force 150 to the puncture mechanism 130. Initially, the alignment guide 132 and the puncture member 135 advance as a unit to the position shown in FIG. 1B. In this position, the seating surface 133 contacts the capsule 125 to center the capsule 125 on the alignment guide 132. For example, a user may press against a surface of the puncturing mechanism 130 to cause the puncturing mechanism 130 to slide within the housing 105. By continuing to apply the force 150, the puncture member 135 is advanced into and through the wall of the capsule 125, as shown in FIG. 1C. The puncture member may comprise one or more sharpened tips 152 to facilitate the advancement through the wall of the capsule 125. The puncturing mechanism 130 is then retracted to the position shown in FIG. 1D, leaving an opening 160 through the wall of the capsule 125 to expose the pharmaceutical formulation in the capsule 125.

Figure 1E:
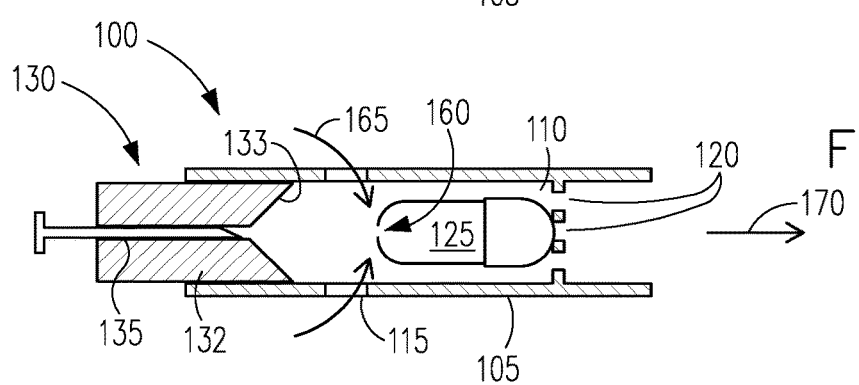
FIG. 1E is a schematic sectional side view of the version of an aerosolization apparatus shown in FIG. 1A in use.

Air or other gas then flows through an inlet 115, as shown by arrows 165 in FIG. 1E. The flow of air causes the pharmaceutical formulation to be aerosolized. When the user inhales 170 through the end section 140 the aerosolized pharmaceutical formulation is delivered to the user's respiratory tract. In one version, the air flow 165 may be caused by the user's inhalation 170. In another version, compressed air or other gas may be ejected into the inlet 115 to cause the aerosolizing air flow 165.

Proper creation of the opening 160 in the capsule 125 allows for efficient and effective delivery of the aerosolized pharmaceutical formulation to the user. In contrast, improper creation of the opening 160 can lead to inefficient and less effective delivery of the medicament to a user. Therefore a properly sharpened tip 152 can help in the creation of consistent openings in the capsule. Also, it is important to have the sharpened tip 152 properly aligned with the capsule 125 to assure proper creation of the opening 160.

Accordingly, to increase the efficiency and effectiveness of the aerosolization apparatus 100, the alignment guide 132 may be designed to improve capsule alignment. In one version, the seating surface 133 is positioned so that at least a portion of the surface is at an angle, a, relative to a transverse axis of greater than 35 degrees, more preferably from 35 degrees to 55 degrees, more preferably from 40 degrees to 53 degrees, and most preferably about 45 degrees. Conventional alignment guides, such as those available from PH&T Pharma in Milan, Italy, and those described in PCT application WO 02/083220 which is incorporated herein by reference in its entirety, have an angle, a, less than 33 degrees. The increased angle, a, of the seating surface 133 provides a decreased angle, b, relative to the longitudinal axis of the capsule 125 and/or the longitudinal axis of the chamber 110 and/or the longitudinal axis of the puncture member 135. The angle, b, of the seating surface 133 relative to one or more of these axes is preferably less than 55 degrees, more preferably from 35 degrees to 55 degrees, more preferably from 37 degrees to 50 degrees, and most preferably about 45 degrees. It has been unexpectedly discovered, that the increased angle, a, of the seating surface 133 significantly improves capsule alignment and unexpectedly extends the effective lifetime of the aerosolization apparatus 100.

A version of an aerosolization apparatus 100 comprising an alignment guide 132 according to the present invention is shown in FIGS. 2A through 2E. In this version, the housing 105 of the aerosolization apparatus 100 comprises a body 205 and a removable endpiece 210. The endpiece 210 may be removed from the body 205 to insert a capsule 125 in the chamber 110 which is formed when the body 205 and the endpiece 210 are connected together. The endpiece 210 comprises a partition 215 that blocks the forward end of the chamber 110, and the partition 215 has the one or more outlets 120 extending therethrough. An example of an aerosolization apparatus with a partition 215 and chamber 110 is described in U.S. Pat. No. 4,069,819 and in U.S. Pat. No. 4,995,385, both of which are incorporated herein by reference in their entireties. In such an arrangement, the chamber 110 comprises a longitudinal axis that lies generally in the inhalation direction, and the capsule 125 is insertable lengthwise into the chamber 110 so that the capsule's longitudinal axis may be parallel to the longitudinal axis of the chamber 110. In the version of FIGS. 2A through 2E, the chamber 110 is sized to receive a capsule 125 containing a pharmaceutical formulation in a manner which allows the capsule to move within the chamber 110. The inlets 115 comprise a plurality of tangentially oriented slots 220. When a user inhales 170 through the endpiece 210, outside air is caused to flow through the tangential slots 220 as shown by arrows 225 in FIG. 2E. This airflow 225 creates a swirling airflow within the chamber 110. The swirling airflow causes the capsule 125 to contact the partition 215 and then to move within the chamber 110 in a manner that causes the pharmaceutical formulation to exit the capsule 125 and become entrained within the swirling airflow. In one version, the capsule 125 may rotate within the chamber 110 in a manner where the longitudinal axis of the capsule is remains at an angle less than 80 degrees, and preferably less than 45 degrees from the longitudinal axis of the chamber. The movement of the capsule 125 in the chamber 110 may be caused by the width of the chamber 110 being less than the length of the capsule 125. In one specific version, the chamber 110 comprises a tapered section 230 that terminates at an edge 235. During the flow of swirling air in the chamber 110, the forward end of the capsule 125 contacts and rests on the partition 215 and a sidewall of the capsule 125 contacts the edge 235 and slides and/or rotates along the edge 235. This motion of the capsule is particularly effective in forcing a large amount of the pharmaceutical formulation through one or more openings 160 in the rear of the capsule 125.

Figure 2A:
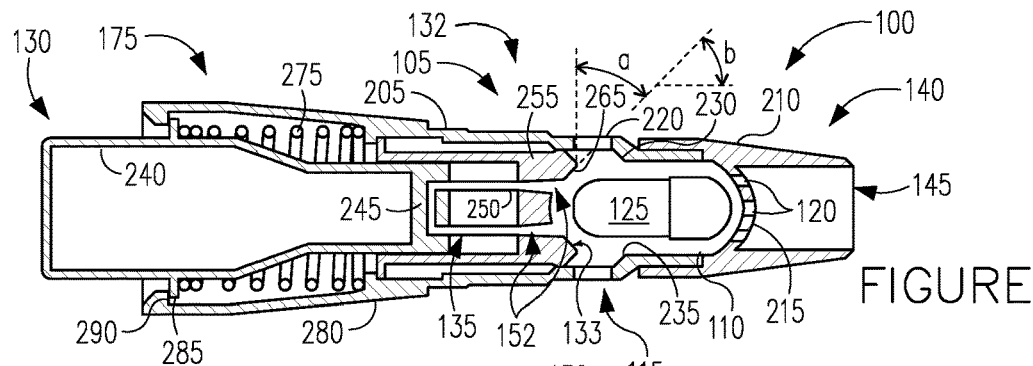
FIG. 2A is a schematic sectional side view of another version of an aerosolization apparatus in a rest position.
Figure 2B:
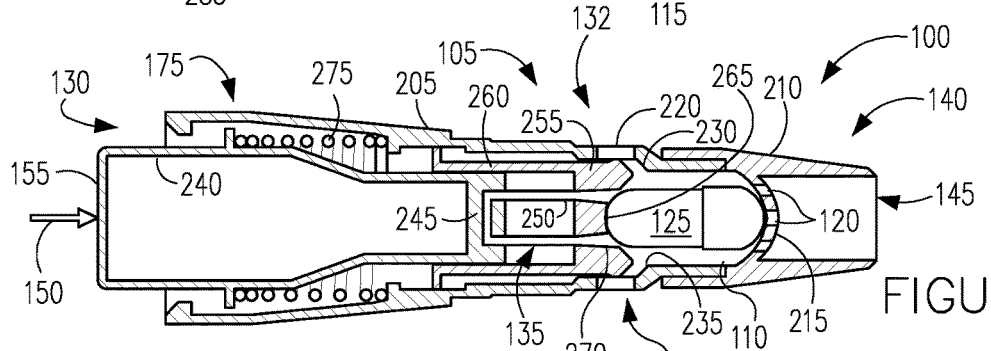
FIG. 2B is a schematic sectional side view of the version of an aerosolization apparatus shown in FIG. 2A just before capsule puncture.
Figure 2C:
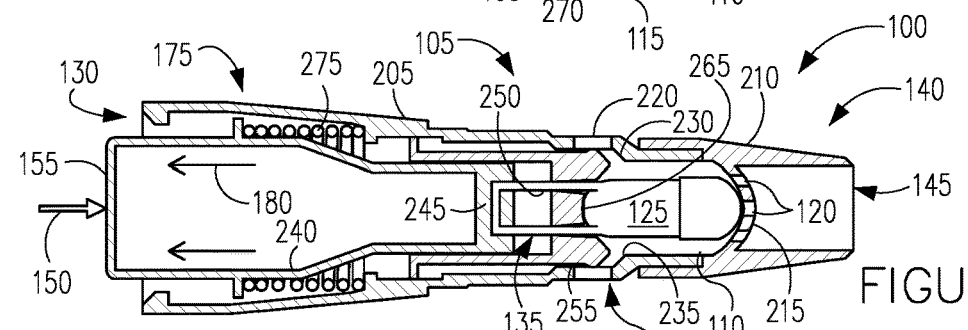
FIG. 2C is a schematic sectional side view of the version of an aerosolization apparatus shown in FIG. 2A as the capsule is being punctured.
Figure 2D:
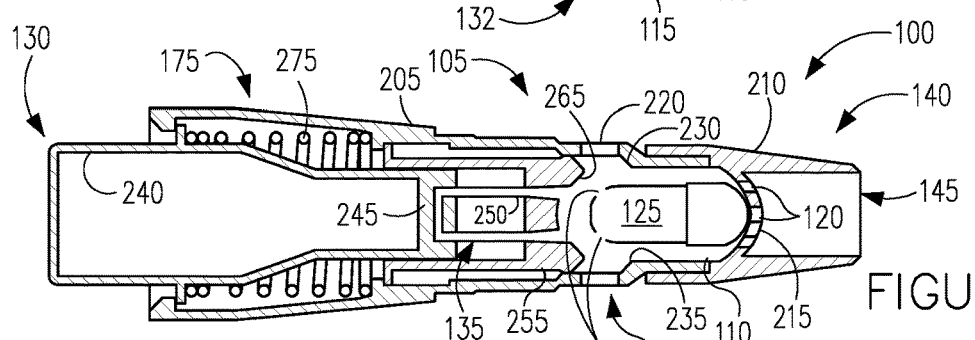
FIG. 2D is a schematic sectional side view of the version of an aerosolization apparatus shown in FIG. 2A just after capsule puncture.
Figure 2E:
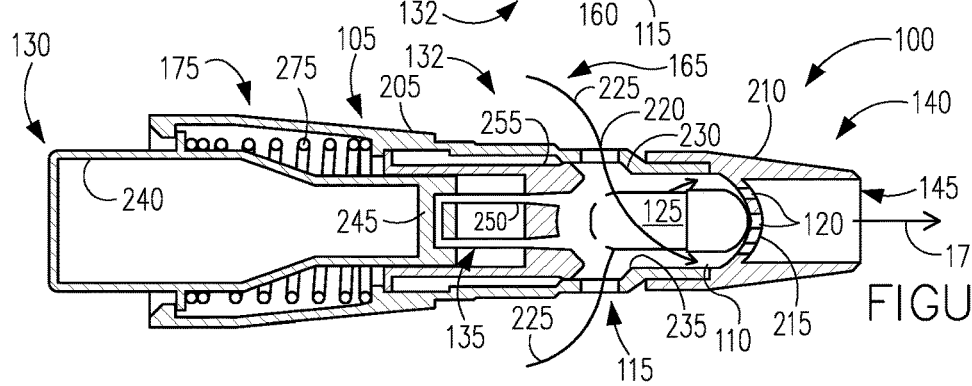
FIG. 2E is a schematic sectional side view of the version of an aerosolization apparatus shown in FIG. 2A in use.

The one or more openings 160 in the rear of the capsule 125 in the version of FIGS. 2A through 2E are created by a puncturing mechanism 130 having a puncture member 135 such as any of those described above that is slidable within the body 205. The puncturing mechanism 130, shown in its rest position in FIG. 2A, comprises a plunger 240 attached at its forward end 245 to the puncture member 135, which in the version shown is a U-shaped staple 250 having two sharpened tips 152 as in any version described above or the like. The puncturing mechanism 130 further comprises a alignment member 255 which contacts the plunger 240 and/or the puncture member 135 and is slidable relative to the plunger 240 and the puncture member 135. To create the openings 160 in the capsule 125, the user applies a force 150 to the plunger 240, as shown in FIG. 2B, such as by pressing against the end surface 155 of the plunger 240 with the user's finger or thumb. The force 150 causes the plunger to slide within the body 205. A slight frictional contact between the plunger 240 the a rear section 260 of the alignment member 255 causes the alignment member 255 to also slide within the body 205 until a forward seating surface 265 of the alignment member 255 contacts the capsule 125, as shown in FIG. 2B. The forward seating surface 265, which may be angled at an angle, a, as discussed above, contacts capsule 125 and secures the capsule 125 between the alignment member 255 and the partition 215. The continued application of force 150 causes the plunger 240 and the puncture member 135 to slide relative to the alignment member 255, as shown in FIG. 2C, to advance the puncture member 135 through openings 270 in the forward seating surface 265 and into the capsule 125. Upon the removal of the force 150, a spring 275 or other biasing member urges the puncturing mechanism 130 back to its rest position. For example, the spring 275 may contact a shoulder 280 in the body 205 and press a flange 285 on the plunger 240 toward a rim 290 in the body 205. The frictional engagement between the plunger 240 and the alignment member 255 also returns the alignment member 255 to its retracted position when the plunger is returned to its retracted position.

In another version, the aerosolization apparatus 100 may be configured differently than as shown in FIGS. 1A through 1D and 2A through 2E. For example, the chamber 100 may be sized and shaped to receive the capsule 125 so that the capsule 125 is orthogonal to the inhalation direction, as described in U.S. Pat. No. 3,991,761. As also described in U.S. Pat. No. 3,991,761, the puncturing mechanism 130 may puncture both ends of the capsule 125. In such version, the puncture member 135 of the present invention may be provided to puncture one or both ends of the capsule 125. In another version, the chamber may receive the capsule 125 in a manner where air flows through the capsule 125 as described for example in U.S. Pat. No. 4,338,931 and in U.S. Pat. No. 5,619,985. In another version, the aerosolization of the pharmaceutical formulation may be accomplished by pressurized gas flowing through the inlets, as described for example in U.S. Pat. Nos. 5,458,135, 5,785,049, and 6,257, 233, or propellant, as described in PCT Publication WO 00/72904 and U.S. Pat. No. 4,114,615. All of the above references being incorporated herein by reference in their entireties.

Figure 3:
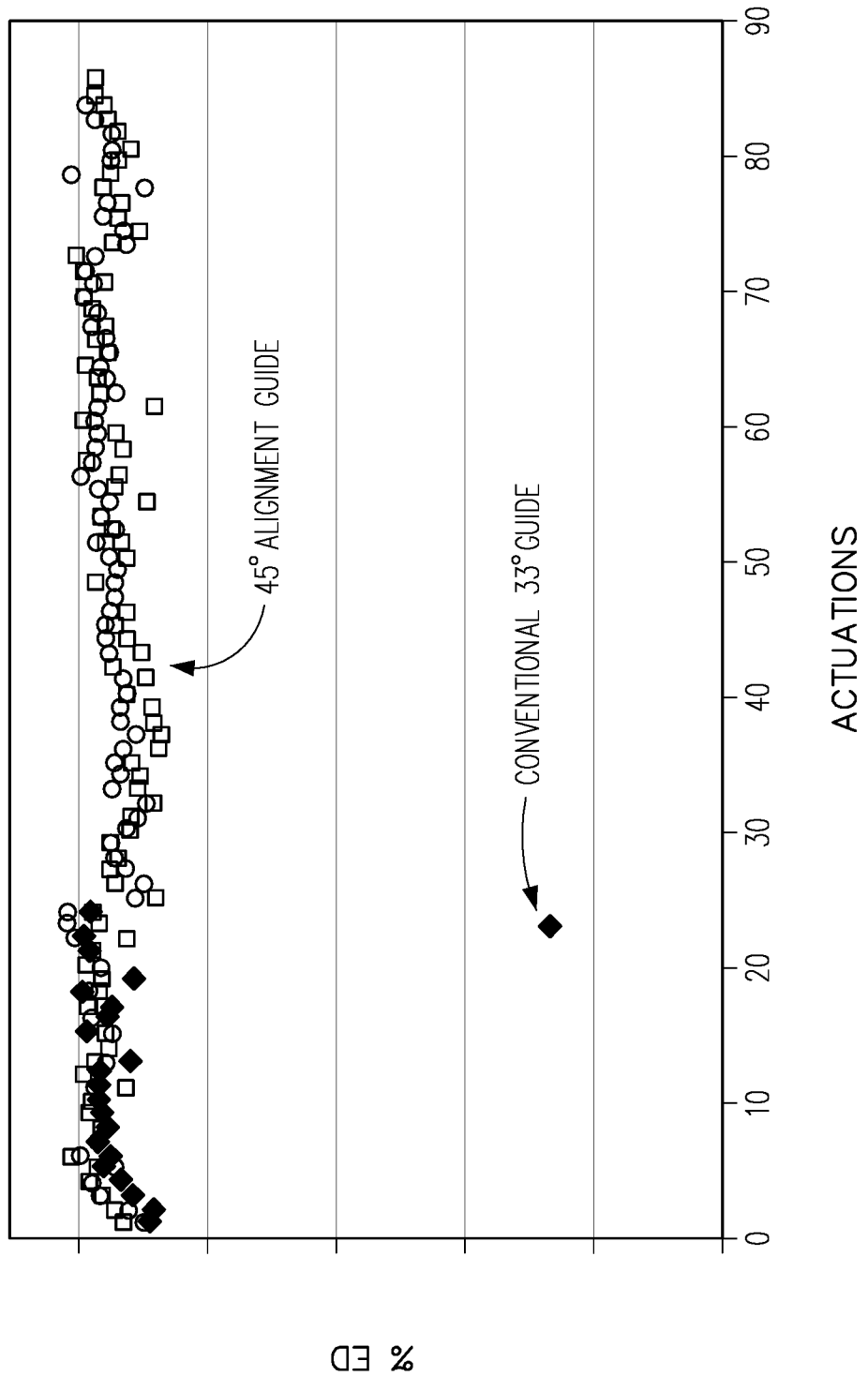
FIG. 3 is a graph showing the effectiveness of using an alignment guide according to the present invention.

FIG. 3 graphically illustrates the advantages using an alignment guide 132 according to the present invention. The diamonds show the resulting emitted dose using a conventional alignment guide having a seating surface with an angle, a, less than 33 degrees. As can be seen, the device loses effectiveness after about 20 actuations. However, the alignment guide having a seating surface having an angle, a, of about 45 degrees provides effective use even after 80 actuations, as shown by the circles and squares.

Figure 4:
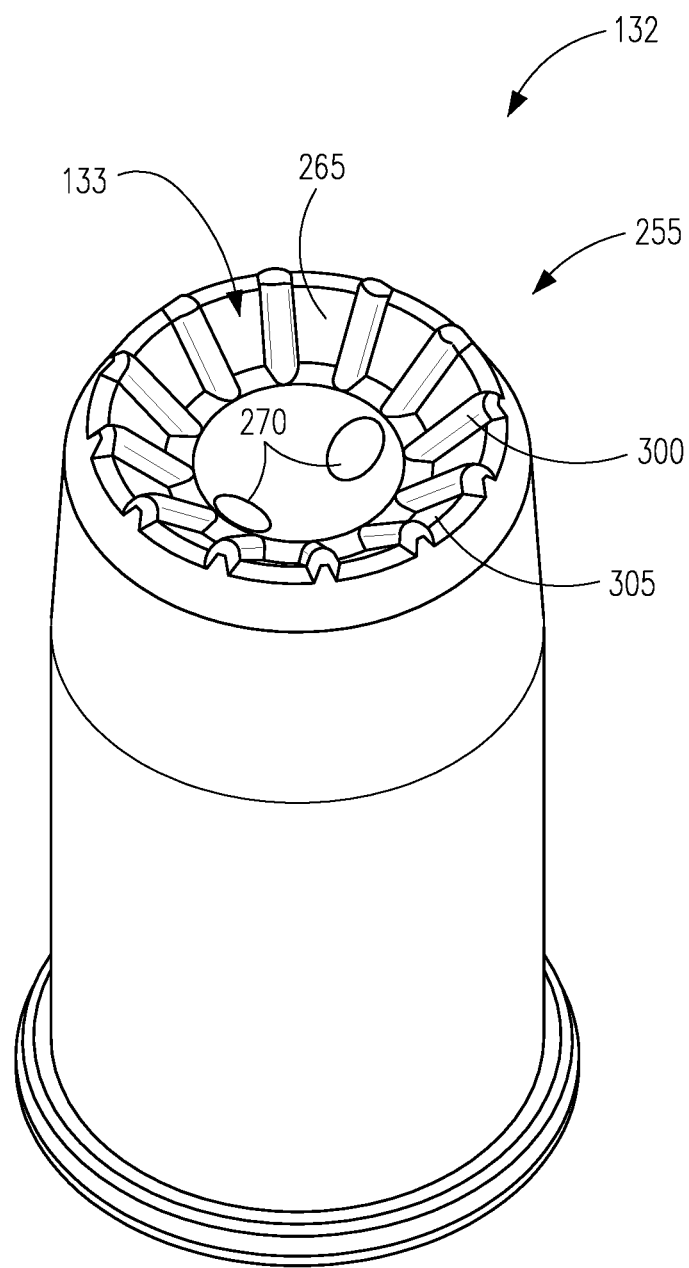
FIG. 4 is a schematic perspective view of a version of an alignment guide.

Another version of an alignment guide 132 is shown in FIG. 4. In this version, the seating surface 133 comprises one or more protrusions, such as ribs 300, that serve to contact the capsule during the puncturing process. The ribs 300 create troughs 305 into which residual powder pharmaceutical formulation may deposit. By providing the troughs 305 and thereby reducing the amount of residual powder on the portion of the seating surface 133 that contacts the capsule, the effectiveness of the aerosolization apparatus is improved and the lifetime of the aerosolization apparatus is extended. The ribs 300 may extend longitudinally, as shown, and/or may extend in an orthogonal direction. In one version, longitudinally extending ribs 300, as shown, are at an angle, a, as described above. The surface of the seating surface 133 and/or the ribs 300 may comprise a low friction material to further reduce the wear on the surface. Alternatively or additionally, the protrusions may be in the form of other raised portions such as bumps and/or the troughs may be formed by indentations, such as divots or valleys, into the surface.

In a preferred version, the invention provides a system and method for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycm, andazithramycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, flcroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, caprcomycin, bacitracin, penems; penicillins including penicilinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefopcrazone, cefotetan, cefmetazoie, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that we delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of; active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperature (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention) which may also function in a buffeting capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymetic excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical for may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

In one version, as discussed above, the pharmaceutical formulation may be contained within a capsule 125. The capsule 125 may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose polyethyleneglycol-compounded HPMC, hydroxypropylcellulose, agar, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical formulation. The sizes generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. Nos. 4,846,876, 6,357,490, and in the PCT application WO 00/07572 published on Feb. 17, 2000, all of which are incorporated herein by reference in their entireties.

Although the present invention has been described in considerable detail, with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization apparatus comprising:
   a housing defining a chamber having one or more air inlets, the chamber being sized to receive a capsule which contains an aerosolizable pharmaceutical formulation;
   a puncturing mechanism within the housing, the puncturing mechanism comprising an alignment guide and a plunger comprising a proximal end configured to be contacted by a user to actuate the apparatus and a distal end including a puncture member, wherein the alignment guide comprises a surface adapted to contact the capsule while the puncture member is advanced into the capsule to create an opening in the capsule, wherein the surface comprises:
      at least one passageway, wherein the puncture member is configured to slide within the passageway;
      one or more protrusions; and
      one or more troughs,
      wherein the one or more protrusions are configured to direct residue of the aerosolizable pharmaceutical formulation to the one or more troughs after an opening is created in the capsule;
   a biasing member arranged between and in contact with the plunger and the housing, the biasing member configured to bias the plunger proximally, away from the chamber; and
   an end section associated with the housing, the end section sized and shaped to be received in a user's mouth or nose so that the user may inhale through the end section to inhale aerosolized pharmaceutical formulation that has exited the capsule through the opening created in the capsule, and
   wherein the surface is configured to be advanced within the housing to contact the capsule prior to the puncturing member being advanced into the capsule.

2. The aerosolization apparatus of claim 1, wherein at least a portion of the surface is sloped at an angle which is less than 55 degrees relative to a longitudinal axis of the chamber.

3. The aerosolization apparatus of claim 1, wherein the surface comprises at least a second passageway, wherein the puncture member is configured to also slide within the at least a second passageway.

4. The aerosolization apparatus of claim 1, wherein the one or more inlets are shaped to create a swirling airflow within the chamber.

5. The aerosolization apparatus of claim 1, wherein the aerosolization apparatus further includes the capsule containing the aerosolizable pharmaceutical formulation and the puncturing mechanism is configured to create one or more openings in a convex end of the capsule.

6. The aerosolization apparatus of claim 1, the capsule comprising at least two convex ends, wherein the puncturing mechanism is configured to create one or more openings in only one of the at least two convex ends of the capsule.

7. The aerosolization apparatus of claim 1, wherein the puncturing mechanism is configured to create two openings in a convex end of the capsule.

8. The aerosolization apparatus of claim 1, wherein the aerosolization apparatus further includes the capsule containing the aerosolizable pharmaceutical formulation and the aerosolizable pharmaceutical formulation comprises an aminoglycoside.

9. The aerosolization apparatus of claim 1, wherein the aerosolization apparatus further includes the capsule containing the aerosolizable pharmaceutical formulation and the aerosolizable pharmaceutical formulation comprises tobramycin.

10. The aerosolization apparatus of claim 1, wherein the aerosolization apparatus further includes the capsule containing the aerosolizable pharmaceutical formulation and the aerosolizable pharmaceutical formulation comprises ciprofloxacin.

11. The aerosolization apparatus of claim 1, wherein the aerosolization apparatus further includes the capsule containing the aerosolizable pharmaceutical formulation and the aerosolizable pharmaceutical formulation comprises amphotericin B.

12. A method of administering an aerosolizable pharmaceutical formulation to a patient, comprising:
    inserting, into the chamber of an apparatus according to claim 1, a capsule containing an aerosolizable pharmaceutical formulation;
    contacting the capsule with the surface of the alignment guide,
    advancing the puncture member through a wall of the capsule to create an opening in the capsule; and
    administering the pharmaceutical formulation to the patient via inhalation.

13. The method of claim 12, wherein inhalation by the patient causes air to flow into the chamber to aerosolize the pharmaceutical formulation.

14. The method of claim 12, wherein at least a portion of the puncture member is advanced through at least one passageway in the surface.

15. The method of claim 14, wherein at least a portion of the puncture member is advanced through at least a second passageway in the surface.

16. The method of claim 13, wherein the aerosolizable pharmaceutical formulation comprises an aminoglycoside.

17. The method of claim 13, wherein the aerosolizable pharmaceutical formulation comprises tobramycin.

18. A method of aerosolizing a pharmaceutical formulation, the method comprising:
    providing an aerosolization apparatus comprising:
        a housing defining a chamber having one or more air inlets, the chamber being sized to receive a capsule which contains an aerosolizable pharmaceutical formulation;
        a puncturing mechanism within the housing, the puncturing mechanism comprising an alignment guide and a plunger comprising a proximal end configured to be contacted by a user to actuate the apparatus and a distal end including a puncture member, wherein the alignment guide comprises a surface adapted to contact the capsule while the puncture member is advanced into the capsule to create an opening in the capsule, wherein the surface comprises:
            at least one passageway, wherein the puncture member is configured to slide within the passageway;
            one or more protrusions; and
            one or more troughs,
            wherein the one or more protrusions are configured to direct residue of the aerosolizable pharmaceutical formulation to the one or more troughs after an opening is created in the capsule;
        a biasing member arranged between and in contact with the plunger and the housing, the biasing member configured to bias the plunger proximally, away from the puncturing mechanism; and
        an end section associated with the housing, the end section sized and shaped to be received in a user's mouth or nose so that the user may inhale through the end section to inhale aerosolized pharmaceutical formulation that has exited the capsule through the opening created in the capsule, and
    wherein the surface is configured to be advanced within the housing to contact the capsule prior to the puncturing member being advanced into the capsule
    inserting a capsule containing an aerosolizable pharmaceutical formulation in the chamber;
    contacting the capsule with the surface of the alignment guide;
    advancing the puncture member through a wall of the capsule to create an opening in the capsule;
    aerosolizing the pharmaceutical formulation in the capsule by flowing air through the chamber; and
    administering the aerosolized pharmaceutical formulation to the respiratory tract of the user during the user's inhalation.

19. The method of claim 18, wherein the user's inhalation causes the air to flow through the chamber.

20. The method of claim 18, wherein the aerosolizable pharmaceutical formulation comprises tobramycin.

* * * * *